United States Patent [19]

Ryan et al.

[11] Patent Number: 4,979,402
[45] Date of Patent: Dec. 25, 1990

[54] ALIQUOTING OF SERIAL LIQUID SAMPLES

[76] Inventors: Will G. Ryan, 906 S. Laflin, Chicago, Ill. 60607; Norman E. Bullock, 5166 Lippincott Rd., Lapeer, Mich. 68446

[21] Appl. No.: 296,424

[22] Filed: Jan. 12, 1989

Related U.S. Application Data

[63] Continuation-in-part of Ser. No. 148,927, Jan. 27, 1988, Pat. No. 4,854,182.

[51] Int. Cl.⁵ .......................... G01N 1/18; G01N 1/28
[52] U.S. Cl. .................................... 73/863; 73/864.51; 73/864.64; 422/102; 128/762
[58] Field of Search ........... 73/864.64, 864.63, 864.51, 73/864.91, 863; 422/100, 102, 103; 128/760–771; 436/174, 180

[56] References Cited

U.S. PATENT DOCUMENTS

| | | | |
|---|---|---|---|
| 2,667,075 | 1/1954 | Blum et al. | 73/864.63 |
| 3,024,660 | 3/1962 | Tothill | 73/864.64 X |
| 3,405,706 | 10/1968 | Cinqualbre . | |
| 3,545,932 | 12/1970 | Gilford | 141/67 X |
| 3,561,427 | 2/1971 | Profy | 73/219 X |
| 3,595,086 | 7/1971 | Bonnet et al. . | |
| 3,730,352 | 5/1973 | Cohen et al. | 210/332 |
| 3,785,928 | 1/1974 | Kessler | 195/140 |
| 3,901,653 | 8/1975 | Jones et al. | 73/864.34 X |
| 3,963,151 | 6/1976 | North, Jr. | 222/309 |
| 4,004,884 | 1/1977 | Zdrodowski | 137/625.12 X |
| 4,025,311 | 5/1977 | Buchinski | 222/373 X |
| 4,042,337 | 8/1977 | Griffith . | |
| 4,126,043 | 11/1978 | Schurmann | 141/34 X |
| 4,227,413 | 10/1980 | Blum . | |
| 4,710,474 | 12/1987 | Malone et al. | 436/178 X |
| 4,847,205 | 7/1989 | Burtis et al. | 422/102 X |
| 4,852,560 | 8/1989 | Hermann, Jr. et al. | 128/76.2 |
| 4,854,182 | 8/1989 | Ryan et al. | 73/864.64 |
| 4,865,813 | 9/1989 | Leon | 422/102 X |
| 4,889,692 | 12/1989 | Holtzman | 422/103 X |

FOREIGN PATENT DOCUMENTS

| | | |
|---|---|---|
| 0052495 | 5/1982 | European Pat. Off. . |
| 0057110 | 8/1982 | European Pat. Off. . |
| 58488 | 9/1891 | Fed. Rep. of Germany . |
| 1302145 | 4/1987 | U.S.S.R. . |
| 1205564 | 9/1970 | United Kingdom . |

*Primary Examiner*—Tom Noland
*Attorney, Agent, or Firm*—Thomas W. Speckman; Douglas H. Pauley

[57] ABSTRACT

An apparatus and process for obtaining an aliquot of serial liquid samples. A measured aliquot of each serial liquid sample is obtained and passed to an aliquot storage chamber with discard of the remainder of each liquid sample. A liquid collection container is provided sufficiently large for the largest single liquid serial sample with a generally vertical aliquot measurement container forming at least one aliquot measurement chamber. Each aliquot measurement chamber has a cross-sectional area in the same relation to the cross-sectional area of the liquid collection chamber as the quantity of each aliquot that is desired to bear to the liquid samples. The bottom of each aliquot measurement container is in the same general horizontal plane as the bottom of the liquid collection container. In one embodiment, the apparatus and process is operated by an aliquot valve which in a first position places each aliquot measurement chamber in communication only with the liquid collection chamber and when in a second position, places each aliquot measurement chamber in communication only with a corresponding aliquot storage chamber.

64 Claims, 5 Drawing Sheets

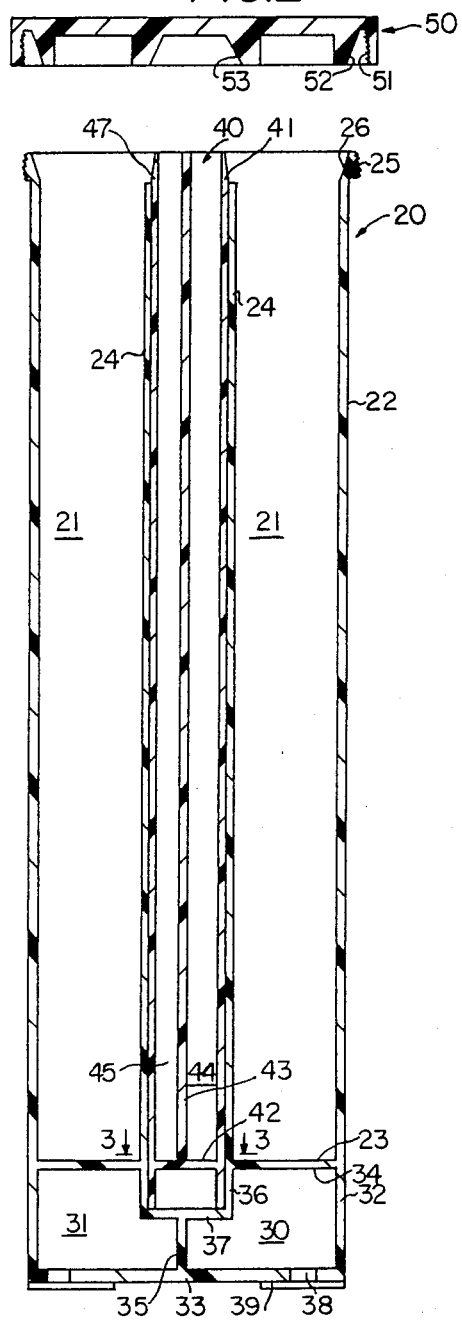
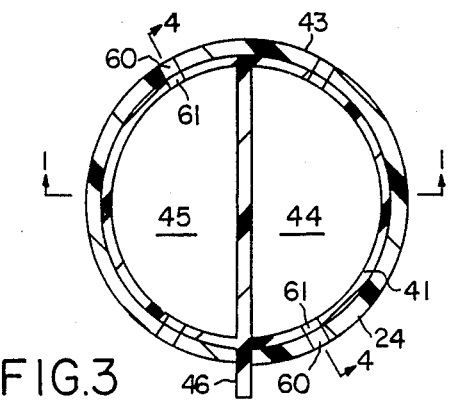
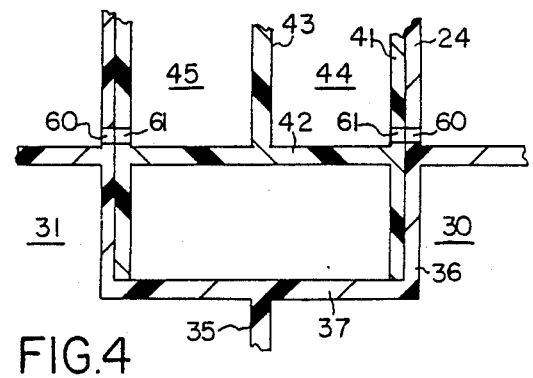
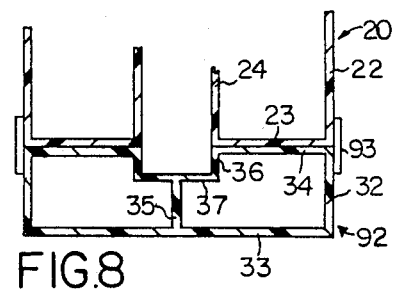
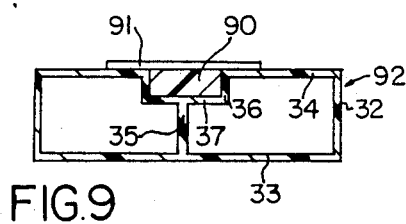

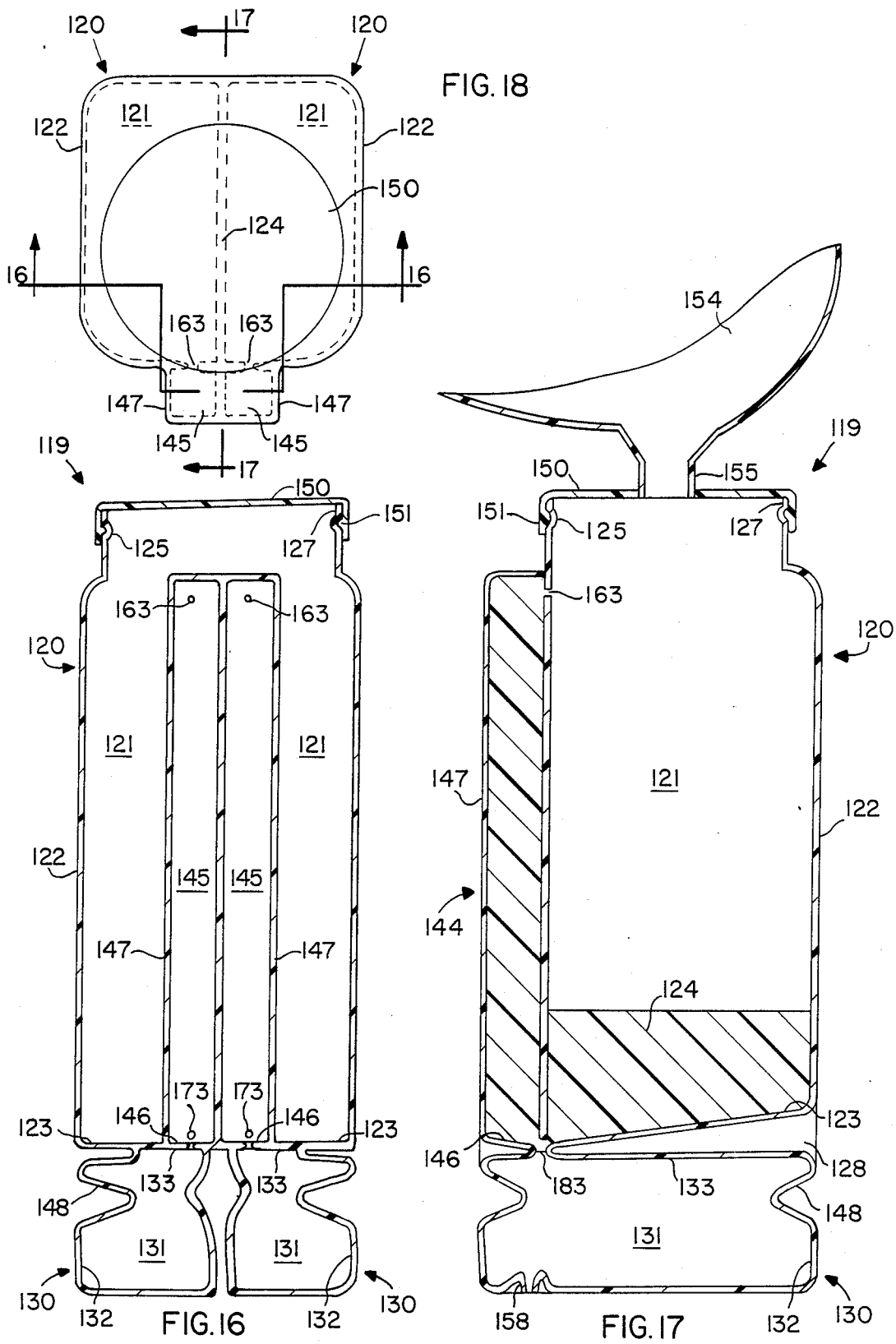

ALIQUOTING OF SERIAL LIQUID SAMPLES

CROSS REFERENCE TO RELATED APPLICATION

This application is a continuation-in-part of my co-pending application, Ser. No. 148,927, filed Jan. 27, 1988 and now U.S. Pat. No. 4,854,182.

BACKGROUND OF THE INVENTION

1. Field of the Invention

This invention relates to an apparatus and process for obtaining a percentge aliquot of serial liquid samples having a constant or variable volume. Aliquoting of serial liquid samples is desired for many testing routines to provide a mixed fraction of each of a series of samples for a single test routine.

2. Description of the Prior Art

It is frequently desirable for plant quality control or for other testing procedures to obtain a single fractional amount of a series of liquid samples. For example, the laboratory analysis of urine specimens is often a standard procedure in the diagnosis and treatment of various human diseases and ailments, as well as to determine the overall well-being of human bodily functions or the determination of improper functioning of one or more of the processes of the body, organs, glands or systems. The collection and analysis of urine specimens is practiced universally throughout the health delivery industry. While the medical profession has developed and adopted a variety of sophisticated methods and test procedures in the analysis and reporting of data of urine specimens, the routine collection methods have not improved. Many medical analyses require the patient to collect all urine excreted during a 24-hour period. The present method of such collection requires collecting each sample in a container and then transferring each sample to a sufficiently large container to accommodate the entire 24-hour series of samples or directly adding each sample to the large container. Therefore, the large container must be maintained in proximity to the person being sampled for the entire 24-hour period which is often inconvenient since 24-hour urine samples are frequently needed from active persons engaging in normal activities. To say the least, this method of sample collection of serial samples is inconvenient for the patient throughout the 24-hour day. Frequently, hydrochloric acid or other preservative must be used in connection with maintaining the samples over the 24-hour period and the patient must be cautioned about touching the liquid preservative. In other instances, the samples must be kept cool to prevent growth of bacteria and the patient may be required to refrigerate all of the samples collected over the 24-hour period. The large container must then be returned to the doctor's office, hospital or other sampling center, where laboratory tests are conducted. Normally, the laboratory tests require only about 1 to about 3 percent of the total collection volume. These small amounts are measured and removed from the large serial collection volume and the remainder of the collection volume is then discarded.

A further problem with current liquid sampling techniques as described above has been that in practice, more than one 24-hour specimen is often required of a patient, and frequently the different samples are required to be subjected to different or no preservatives. In these cases, it is the present practice to perform sequential sampling, that is repeat the process, which has the disadvantage that the second tests are performed on samples which may be very different from the first tests due to various bodily functions and thus the test results are not validly comparable.

SUMMARY OF THE INVENTION

It is an object of this invention to overcome many of the above disadvantages of serial liquid sampling.

It is an object of this invention to provide percentage aliquoting of each serial liquid sample of a constant or variable volume at the time it is taken, storage of only the aliquot amount, and discard of the remainder of each serial liquid sample, thereby providing much smaller and more convenient sampling containers.

It is another object of this invention to provide one aliquot amount or a plurality of aliquot amounts obtained from a single series of liquid samples.

It s still a further object of this invention to provide one aliquot amount storage chamber or a plurality of aliquot amount storage chambers which may contain different preservatives or no preservative for the different aliquot amount storage chambers, corresponding to testing procedures.

It is yet another object of this invention to provide an effective antibiotic preservative to one or more aliquot storage chambers to effectively preserve the aliquot amount in the aliquot storage chamber.

In one embodiment according to this invention, the above objects of this invention and further features which will become apparent are achieved by a liquid aliquoting apparatus for obtaining an aliquot of a series of liquid samples. The apparatus comprises a liquid collection container forming a liquid collection chamber; an aliquot container forming at least one aliquot storage chamber below the liquid collection chamber; a generally vertical aliquot tube forming at least one aliquot measurement chamber, each aliquot measurement chamber having a cross-sectional area in the same relation to the cross-sectional area of the liquid collection chamber as the quantity of each aliquot is desired to bear to the liquid samples. The aliquot measurement chamber has a bottom in the same general horizontal plane as the bottom of the liquid collection container and aliquot valve means which in a first position places each aliquot measurement chamber in communication only with the liquid collection chamber and when in a second position places each aliquot measurement chamber in communication only with a corresponding aliquot storage chamber.

In preferred embodiments, 2 to about 4 aliquot measurement chambers are provided with a corresponding number of aliquot storage chambers.

Preferred embodiments include the liquid collection chamber and the aliquot storage chambers in a single partitioned outer container having the generally vertically aliquot tube in a central position extending to the top of the liquid collection container, thereby forming an annular liquid collection chamber.

Preferred embodiments incorporate the aliquot valve means as a series of passageways in the lower portion of the aliquot tube and a liquid collection chamber inner side wall whereby rotation of the aliquot tube effects the necessary liquid communication as desired for first passing the liquid from the liquid collection chamber to only the aliquot measurement chamber and then passing the liquid from each aliquot measurement chamber to a corresponding aliquot storage chamber. Other preferred embodiments effect the same liquid communication relationships by a vertical movement, or "push-pull" action, of the aliquot valve in respect to the collection and storage chamber inner side walls.

According to one embodiment of this invention, the process for collecting at least one aliquot of serial liquid samples according to this invention includes the steps sequentially comprising: adding the first of a series of liquid samples to a liquid collection chamber; placing the liquid collection chamber in liquid communication only with at least one generally vertical aliquot measurement chamber, each aliquot measurement chamber having a cross-sectional area in the same relation to the cross-sectional area of the liquid collection chamber as the quantity of the aliquot is desired to bear to the liquid samples, and a bottom in the same general horizontal plane as a bottom of the liquid collection chamber; passing liquid from the liquid collection chamber into the aliquot measurement chamber until the liquid level in the aliquot measurement chamber is equal to the liquid level in the liquid collection chamber forming an aliquot amount in the aliquot measurement chamber; placing the aliquot measurement chamber in liquid communication with a corresponding aliquot storage chamber; passing the aliquot amount from the aliquot measurement chamber to a corresponding aliquot storage chamber; closing the aliquot storage chamber from communication with the aliquot measurement chamber; discharging the remainder of the serial liquid sample from the liquid collection chamber; and repeating the process for the desired number of serial liquid samples.

It is seen that the apparatus and process for aliquoting of serial liquid samples provided by this invention is suitable for obtaining desired fractions of serial liquid samples while storing only the measured fraction amount of each serial sample and discharging the remainder of each sample, and then repeating the process with the next of the series of liquid samples. The successively obtained aliquot measured amounts in the aliquot storage chamber may bear the same fractional relation to the total volume of the series of samples as each aliquot bears to each liquid sample. Therefore, a collection of aliquoted amounts of a large volume from a series of liquid samples may be obtained using an apparatus of sufficient size to measure an aliquot of only the largest volume of the series and of sufficient size to store the total measured aliquot amount of the series. This provides a much smaller apparatus than currently used and further requires preservation of a much smaller volume in the aliquot storage chamber rendering more effective use of different methods of preservation than current sampling methods.

In another preferred embodiment according to this invention, the liquid aliquoting apparatus for obtaining an aliquot of a series of liquid samples includes a liquid collection container which forms a liquid collection chamber. A top portion of the liquid collection container forms an opening having a cross section large enough to accommodate a fluid sample intake into the liquid collection chamber. In one embodiment according to this invention, the cross section of the opening is large enough to facilitate urine intake into the liquid collection container directly from human discharge. One or more aliquot storage containers each form an aliquot storage chamber, preferably below the liquid collection chamber. One or more generally vertical aliquot measurement containers each form an aliquot measurement chamber.

Vent means are positioned near a high point of each aliquot measurement container. Each aliquot measurement chamber is in fluid communication with a corresponding liquid collection chamber through the vent means. In a preferred embodiment of this invention, the vent means include one or more vent ports. Each vent port is sized large enough to allow air to flow through the vent port. Each vent port is sized small enough to retain an aliquot measurement portion of a liquid sample within each aliquot measurement chamber when the liquid aliquoting apparatus is tilted in a position to discharge a liquid collection portion of the liquid sample from the liquid collection chamber. In one embodiment, the vent port has a round cross section with a vent port diameter in the range from about 3/128 inch to 5/128 inch, preferably 1/32 inch.

The liquid aliquoting apparatus has fill means positioned in a region near a low point of each aliquot measurement container. Each aliquot measurement chamber is in fluid communication with the liquid collection chamber through the fill means. In a preferred embodiment of this invention, the fill means include one or more fill ports each sized large enough to allow the liquid sample to seek an equilibrium level within the liquid collection chamber and each aliquot measurement chamber. Each fill port is sized small enough to retain an aliquot measurement portion of the liquid sample within each aliquot measurement chamber when the liquid aliquoting apparatus is tilted in a position to discharge the liquid collection portion of the liquid sample from the liquid collection chamber. The fill port preferably has a round cross section with a fill port diameter in a range from about 3/64 inch to 5/64 inch, preferably about 1/16 inch.

Drain means are positioned at a low point of each aliquot collection chamber and the liquid collection chamber. Each aliquot measurement chamber is in fluid communication with a corresponding aliquot storage chamber. In a preferred embodiment of this invention, the drain means include one or more drain ports each sized small enough to retain the aliquot measurement portion of the liquid sample in each aliquot measurement chamber and the liquid collection chamber. Each drain port is sized large enough to allow the liquid sample to flow through the drain port into each aliquot measuring chamber when a volume displacement means is activated. The drain port preferably has a round cross section with a drain port diameter in a range from about 3/100 inch to about 5/100, preferably about 1/25 inch.

The liquid aliquoting apparatus has volume displacement means for discharging a fluid from each aliquot storage chamber and intaking a liquid sample from each corresponding aliquot measurement chamber. In a preferred embodiment of this invention, the volume displacement means comprises a collapsible aliquot storage container. The aliquot storage container can be collapsed by the aliquot storage container having one or more bellowed sides.

In one embodiment according to this invention, the liquid collection container has a liquid collection container bottom which is sloped downward toward the fill means or fill port. A supporting rib can be secured between the liquid collection bottom and the container top of the liquid collection container. The container top has engaging means for sealably mating the container top with an upper portion of the liquid collection container. The engaging means may comprise the container top having container top threads which are sealably mateable with the upper portion threads of the upper portion.

In another embodiment according to this invention, liquid sample inlet means are attached to the container top and in communication with the liquid collection chamber. The liquid sample inlet means may comprise a funnel having a convergent end sealably attached to the container top.

In a preferred embodiment of this invention, graphic instructions are positioned on at least one liquid collection container side of the liquid collection container. The graphic instructions indicate a direction in which the liquid aliquoting apparatus must be tipped in order to retain an aliquot measurement portion of the liquid sample within each aliquot storage chamber. The graphic instructions may include a directional arrow and language displayed on the container for instructing a user how to properly tip and operate the liquid aliquoting apparatus.

In one embodiment of this invention, the bottom and/or side of the aliquot storage container can have access means for accessing the contents of each aliquot storage chamber. The access means may comprise at least one indent or nipple formed in the bottom and/or the side of the aliquot storage container.

In a preferred embodiment of this invention, the overall horizontal cross-sectional shape of the liquid aliquoting apparatus is rectangular. With such rectangular arrangement, one aliquot storage chamber may occupy a corner section of the liquid aliquoting apparatus. In another preferred embodiment according to this invention, the overall horizontal cross-sectional shape of the liquid aliquoting apparatus is round, circular or of another suitable corss-sectional shape.

In a preferred embodiment of this invention, an aliquot measurement volume of each aliquot measurement chamber is in a range from about 1 percent to about 50 percent, preferably about 3 percent to about 5 percent, of a liquid collection volume of the liquid collection chamber.

In one embodiment, an aminoglycoside antibiotic is stored within at least one aliquot storage chamber. The aminoglycoside antibiotic in a liquid form can be evaporated on at least one inner wall surface of the aliquot storage container. The aminoglycoside antibiotic is preferably gentamicin. In the embodiment of this invention having a plurality of aliquot measurement chambers and/or aliquot storage chambers, one or more separating walls are positioned between the walls of the liquid collection container from the liquid collection container bottom up to less than about one-half of the height of the liquid collection chamber. The total number of separating walls forms a number of liquid collection containers equal to the number of aliquot measurement containers.

A process for obtaining an aliquot sample from a liquid aliquoting apparatus according to the embodiment of this invention includes the steps of: introducing a liquid into the liquid chamber; waiting until the liquid in the liquid collection chamber flows into at least one aliquot measuring chamber and further waiting until a level of the liquid sample reaches an equilibrium level within the liquid collection chamber and each aliquot measuring chamber; tipping or tilting the liquid aliquoting apparatus to discharge the liquid within the liquid collection chamber and the remaining aliquot measurement portion of the liquid sample within each aliquot measuring chamber is retained; returning the liquid aliquoting container to a generally vertical and upright position; discharging a fluid from the aliquot storage chamber; and drawing the aliquot measurement portion of the liquid from each aliquot measurement chamber into each corresponding aliquot storage chamber.

It can be readily appreciated that the apparatus and process for obtaining liquid aliquots of a series of liquid samples according to this invention may be readily applied not only to medical applications, but to a wide variety of chemical plant, water, or other liquid testing requirements where a series of liquid samples must be taken for testing.

BRIEF DESCRIPTION OF THE DRAWING

The above and further objects and advantages of this invention will be apparent from the detailed description of further embodiments and by reference to the drawings wherein:

FIG. 1 is a side sectional view of a liquid aliquoting apparatus according to one embodiment of this invention along the section shown as 1—1 in FIG. 3;

FIG. 2 is a side sectional view of the cap for an apparatus as shown in FIG. 1;

FIG. 3 is a top sectional view along the section shown in FIG. 1 and 3—3 showing an aliquot valve means in a first position placing each aliquot measurement chamber in communication only with the liquid collection chamber of the central portion of the apparatus shown in FIG. 1;

FIG. 4 is a partial side sectional view along the section 4—4 shown in FIG. 3;

FIG. 8 is a partial side sectional view of an embodiment of this invention having a removable aliquot storage container;

FIG. 9 is a side sectional view of the aliquot storage container shown in FIG. 8 in a removed position;

FIG. 16 is a cross-sectional front view along line 16—16, as shown in FIG. 18, of a liquid aliquoting apparatus having two aliquot measurement chambers according to another embodiment of this invention;

FIG. 17 is a cross-sectional side view along line 17—17, as shown in FIG. 18, of the liquid aliquoting apparatus as shown in FIG. 16 additionally having a funnel adapter according to one embodiment of this invention; and FIG. 18 is a top view of the liquid aliquoting apparatus as shown in FIGS. 16 and 17.

DESCRIPTION OF PREFERRED EMBODIMENTS

Figure 5:
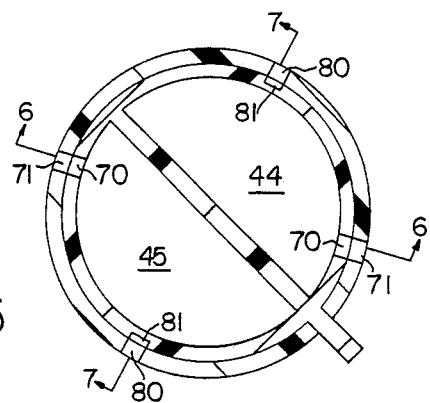
FIG. 5 is a top sectional view corresponding to FIG. 3 showing the aliquot valve means in a second position placing each aliquot measurement chamber in communication only with a corresponding aliquot storage chamber.

Referring to the embodiment of this invention as shown in FIG. 1, a single liquid collection container 20 having outer side wall 22 and bottom side wall 23 together with inner side wall 24 forms annular liquid collection chamber 21. Aliquot storage chambers 30 and 31 are below liquid collection chamber 21 and defined by side walls 32, bottom wall 33, top wall 34, partition wall 35, valve well side walls 36 and valve well bottom wall 37. As shown in FIG. 1, the aliquot storage chambers are within a container contiguous with liquid collection container 20. Round tubular-shaped liquid collection chamber inner side wall 24, while shown in FIG. 1 on a central axis of liquid collection container 20 need not be on such a central axis but may even be adjacent an outer side wall 22. The only restriction in location of the tube formed by inner side wall 24 is access to the desired plurality of aliquot storage chambers below the liquid collection container by the valve means to be described.

Aliquot tube 40 is formed with side walls 41 to fit snugly within the tubular structure formed by liquid collection container inner side wall 24 and bottom wall 42 located to have its top surface in approximately the same plane as bottom wall 23 of liquid collection chamber 21. As shown in FIGS. 1-7, aliquot tube 40 is divided into two aliquot measurement chambers 44 and 45 by partition wall 43. The inner volume of aliquot tube 40 may be divided into any desired number of aliquot measurement chambers to provide the desired number of separate measured aliquot fractions of the series of liquid samples. Each aliquot measurement chamber, such as 44 and 45, should have a cross-sectional area in the same relation to the cross-sectional area of the liquid collection chamber as the quantity of each aliquot amount is desired to bear to the liquid samples in instances where the bottom wall 42 is in approximately the same plane as bottom wall 23. Generally, the cross-sectional area of each aliquot measurement chamber as shown in FIG. 1 is about 1 to about 50 percent the cross-sectional area of the liquid collection chamber, and in medical applications frequently about 1 to about 5 percent. The tube formed by liquid collection chamber inner side wall 24 and the cross-sectional area formed by the inside dimensions of aliquot tube 40 are sized to provide the desired number and size of aliquot amounts of the series of liquid samples. The aliquot measurement chambers within a single aliquot tube may be of the same or of different cross-sectional areas to provide the same or different total aliquot amounts for desired testing. Aliquot tube 40 may be held in desired vertical position in tubular structure 24 by any suitable means, such as "O" rings or detents and grooves or other positioning means known to the art. Likewise, liquid passage between aliquot tube 40 and tubular structure 24 may be restricted by any suitable means known to the art, such as "O" rings, grease seals, and the like.

While the aliquot measurement chambers will generally have constant cross-sectional areas for their collecting length, if it is desired to measure different volume fractions dependent upon the volume of each serial sample, this can be achieved by providing a tapered aliquot measurement chamber having increasing or decreasing cross-sectional area or by curving a constant cross-sectional area tube which may provide greater aliquot fractions at either smaller or larger serial sample volumes. Likewise, the cross-sectional area of the liquid collection chamber may be altered along its length. The basic relationships pointed out above remain between cross-sectional areas of the aliquot measurement chamber and the liquid collection chamber at the same horizontal plane.

Figure 6:
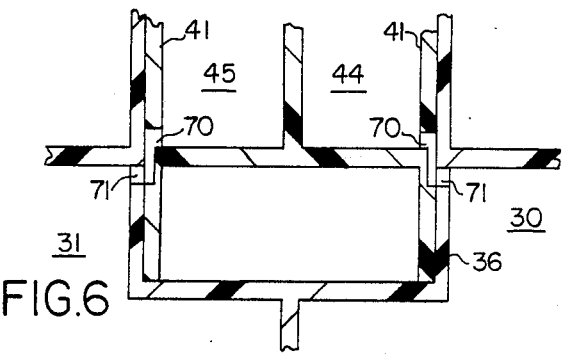
FIG. 6 is a partial side sectional view along the section 6—6 shown in FIG. 5.
Figure 7:
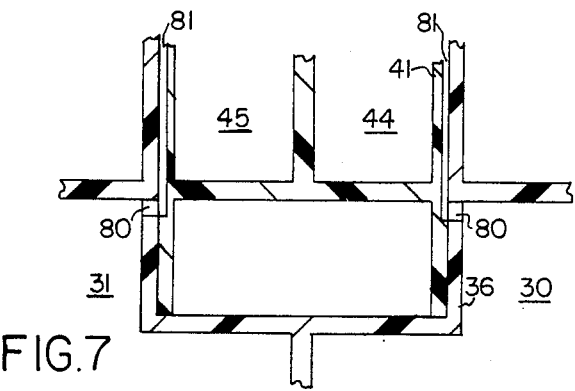
FIG. 7 is a partial side sectional view along the section 7—7 shown in FIG. 5.

In operation, one of the serial liquid samples is added to liquid collection chamber 21. During addition of the serial liquid sample to the liquid collection chamber, or after collection of the serial liquid sample in the liquid collection chamber, the liquid collection chamber is placed in liquid communication with the generally vertical aliquot measurement chambers by rotation of aliquot tube 40 within liquid collection chamber inner side wall 24 by handle 46. As shown in FIGS. 3-7, rotation of aliquot tube 40 within liquid collection chamber inner side wall 24 functions as an aliquot valve as will be explained in more detail. FIGS. 3 and 4 show the aliquot valve in a first position placing each aliquot measurement chamber in communication only with the liquid collection chamber. FIGS. 5-7 show the aliquot valve in a second position placing each aliquot measurement chamber in communication only with a corresponding aliquot storage chambers number 30 and 31. Intermediate positions provide isolation of the aliquot measurement chambers.

The aliquot valve first position as shown in FIGS. 3 and 4 is used in transfer and measurement of an aliquot amount of liquid from the liquid collection chamber 21 to aliquot measurement chambers 44 and 45. As best seen in FIG. 4, aliquot measurement inlet opening 61 in aliquot tube wall 41 is aligned with aliquot measurement inlet opening 60 in liquid collection chamber inner side wall 24. In this position, the liquid will flow from liquid collection chamber 21 to each aliquot measurement chamber 44 and 45 and seek the same levels in the aliquot measurement chambers as in the liquid collection chamber 21, thereby providing a predetermined fraction of the total liquid in liquid collection chamber 21 to the aliquot measurement chambers. In cases where the bottom walls of the aliquot measurement chambers are in approximately the same plane as the bottom wall of the liquid collection chamber, the aliquot fraction amount is directly related to the cross-sectional areas of these chambers. While the aliquot measurement inlet openings 60 and 61 are shown to be adjacent aliquot measurement chamber bottom wall 42 and liquid collection chamber bottom wall 23, it should be readily apparent that these openings may be at any location below the liquid surface of the smallest of the series of liquid samples.

The aliquot valve second position as shown in FIGS. 5-7, is used in transfer of the measured aliquot amount of liquid from the aliquot measurement chambers 44 and 45 to corresponding aliquot storage chambers 30 and 31. As best seen in FIG. 6, aliquot outlet opening 70 in aliquot measurement chamber side wall 41 is aligned with aliquot outlet opening 71 in valve well side wall 36. In this position, the measured aliquot amount will flow from each aliquot measurement chamber to a corresponding aliquot storage chamber, such as from aliquot measurement chamber 44 to aliquot storage chamber 30. To facilitate the liquid flow to the aliquot storage chambers, it is preferred that each aliquot storage chamber be provided with at least one air vent to allow escape of the air with the concomitant liquid filling. One manner of providing such an air vent is through the aliquot valve as shown in FIG. 7. Air outlet opening 80 passes through valve well side wall 36 in communication with air outlet passage 81 in aliquot tube side wall 41 to the top of liquid collection container inner side wall 24 to permit the escape of air from the aliquot storage chambers to the ambient atmosphere.

To assist the user in the proper use of the valve, the aliquot tube 40 to which handle 46 is affixed, may be marked to show the two operating positions of the valve with instructions for each of these operating positions, such as in the first operating position "Fill and Carry Position", and in the second operating position "Sample Transfer Position".

In the above description of the aliquot valve and in the drawings, specific structure has been referred to and it should be readily apparent that these structures may be modified as long as the desired liquid communication and liquid isolation relations are obtained. For example, where reference has been made to single openings, it is readily apparent that multiple openings may be suitable for more rapid operation. Likewise, the positioning of the openings may be varied within limits providing desired liquid communication and isolation.

An important aspect of the invention is in achieving simultaneous multiple measured aliquot amounts from each of a series of liquid samples and transferring the measured aliquot amounts to an aliquot storage chamber allowing disposal of the remainder of the liquid sample from the liquid collection container. This permits use of a small sized liquid collection container and permits measurement and storage of a desired plurality of aliquot amounts, the storage being in separated storage chambers which may be subjected to differing or no preservative or other chemical treatments.

Liquid collection container top 50 is provided for tight closing of liquid collection chamber 21. In one embodiment shown in FIG. 2, liquid collection container top 50 has screw threads 51 engageable with screw threads 25 at the top of liquid collection container outer side wall 22. To further assure tight sealing, sloping surface 52 may be provided to engage receiving surface 26 and sloping surface 53 may be provided to engage receiving surface 47. It is readily apparent that snap-on caps or any other suitable firmly closing top may be used to close liquid collection container 20.

As shown in FIG. 1, it may be desirable to provide aliquot storage chamber access hole 38 to each aliquot storage chamber providing ready access to the individual aliquot storage chamber for removal of the aliquot amount, for further aliquoting of the already measured aliquot amount, for adding chemicals to the aliquot storage chamber for testing or preservation purposes, and the like. This may be achieved by providing any suitable tightly closing cover 39 over aliquot storage chamber access 38, shown in FIG. 1 to be a pressure sensitive tape.

In other embodiments of this invention, the aliquot storage chamber container may be separable from the upper liquid collection container 20 to provide a smaller package, for example, for shipping to an analysis center. In such cases, the top portion or liquid collection container 20 may be discarded or reused on other lower portions or aliquot storage chamber containers. FIG. 8 shows one embodiment providing aliquot container 92 which is removable from liquid collection container 20. The aliquot container and aliquot storage chambers in this embodiment are the same as described with respect to the previous figures except that liquid collection container 20 is provided with a bottom wall 2 separate from top wall 34 of the aliquot storage chambers. Assurance of desired rotary alignment of removable aliquot container 92 with liquid collection container 20 to provide desired operation of the aliquot valve as described above, may be obtained by any suitable means known to the art, such as detents and dimples in the opposing adjacent surfaces of the liquid collection chamber bottom wall and aliquot storage chamber top wall, or by any opposing interlocking means on the outside of side walls 22 and 32. Likewise, any suitable means for tightly fastening removable aliquot container 92 to the bottom of liquid collection container 20 may be used, such as pressure sensitive tape 93 or any clamping or interlocking structure on the exterior of these side walls. FIG. 9 shows removable aliquot container 92 in the removed position with aliquot storage chamber closing plug 90 maintained in position by pressure sensitive sealing tape 91. In such condition, a small sized container may hold measured aliquots of a series of liquid samples and be conveniently transported.

Figure 10:
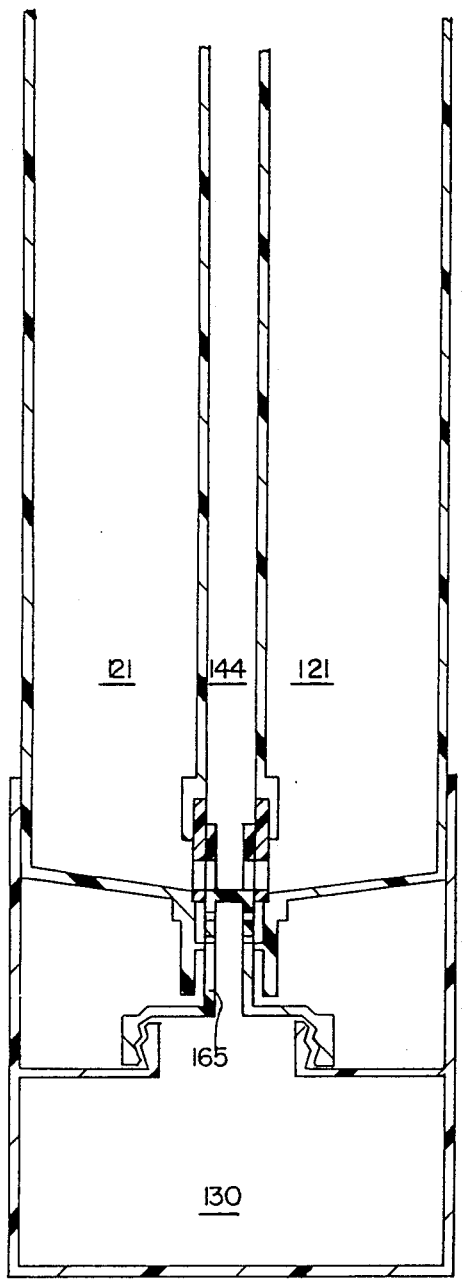
FIG. 10 is a side sectional view of another liquid aliquoting apparatus of this invention.
Figure 11:
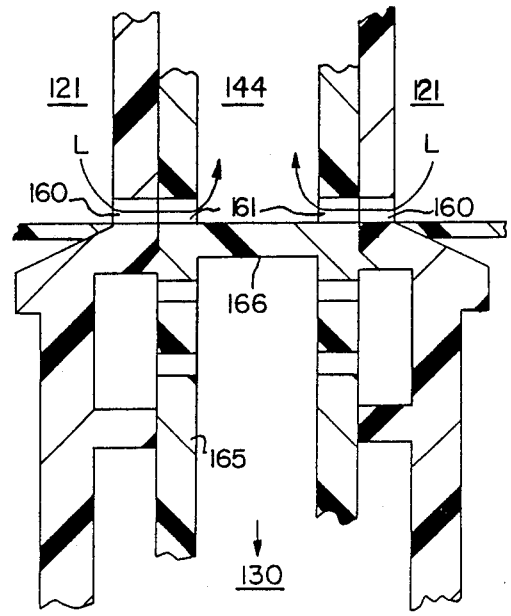
FIG. 11 is a side sectional view showing an aliquot valve means in a first position placing the aliquot measurement chamber in communication only with the liquid collection chamber of the apparatus shown in FIG. 10.
Figure 12:
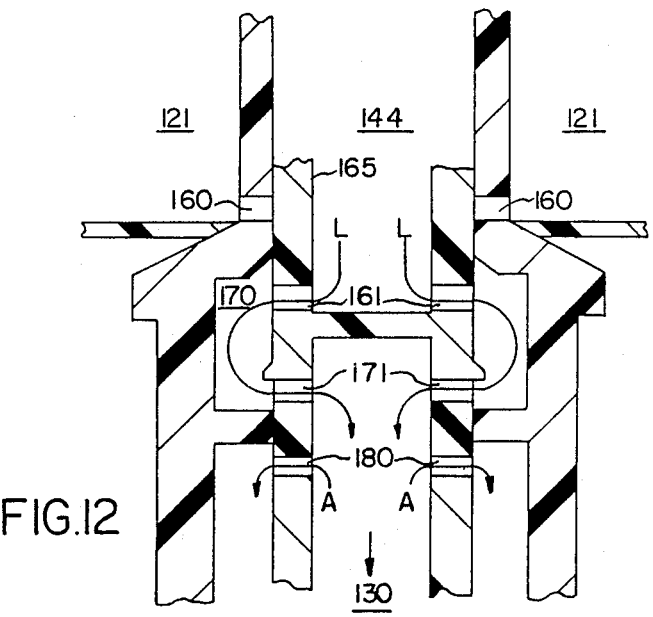
FIG. 12 is a side sectional view corresponding to FIG. 11 showing the aliquot valve means in a second position placing the aliquot measurement chamber in communication only with the aliquot storage chamber.

FIGS. 10 through 12 show another apparatus for aliquoting of serial liquid samples in accordance with this invention. The overall function of the apparatus and method of aliquoting is the same as described above except that a vertically moving "push-pull" valve means is used to provide the necessary liquid communication as described above. FIG. 10 shows the general relation of the push-pull valve means in respect to liquid collection chamber 121, aliquot measurement chamber 144, and aliquot storage chamber 140. FIG. 11 shows push-pull valve 165 as a tubular structure having partition 166 in approximately the same plane as the bottom wall of liquid collection chamber 121 and shows the valve to be in a first position placing aliquot measurement chamber 144 in communication only with liquid collection chamber 121 through openings 160 and 161. In this first position, the liquid passes from liquid collection chamber 121 to aliquot measurement chamber 144, as shown by arrows indicated by "L", and fills to the same level as in liquid collection chamber 121, as described above. Following measurement of the aliquot sample in aliquot measurement chamber 144, valve 165 is depressed, by any suitable means, to the second position shown in FIG. 12. In the second position, aliquot measurement chamber 144 is in liquid communication with aliquot storage chamber 130 through openings 161, chamber 170, and openings 171, with the liquid flowing from aliquot measurement chamber 144 to aliquot storage chamber 130 in the manner shown by arrows labeled "L". To facilitate flow of the measured aliquot amount to aliquot storage chamber 130, air outlets 180 are provided to allow the escape of air to the exterior ambient atmosphere by any suitable means which, upon movement of valve 165 to the first position, closes such air vents. As described more fully above, multiple aliquot measurement chambers with corresponding aliquot storage chambers may be used with modifications to the structure which are readily apparent to one skilled in the art upon reading of this disclosure, or by providing multiple aliquot tubes, valves and collection containers, usually from two to about four.

Figure 14:
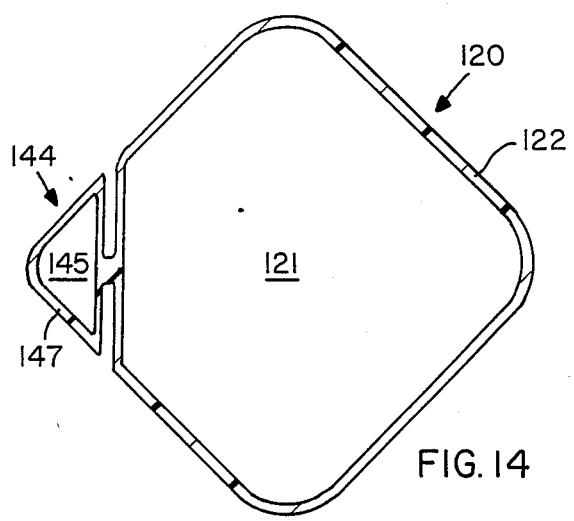
FIG. 14 is a cross-sectional top view of the liquid aliquoting apparatus along line 14—14, as shown in FIG. 13.
Figure 13:
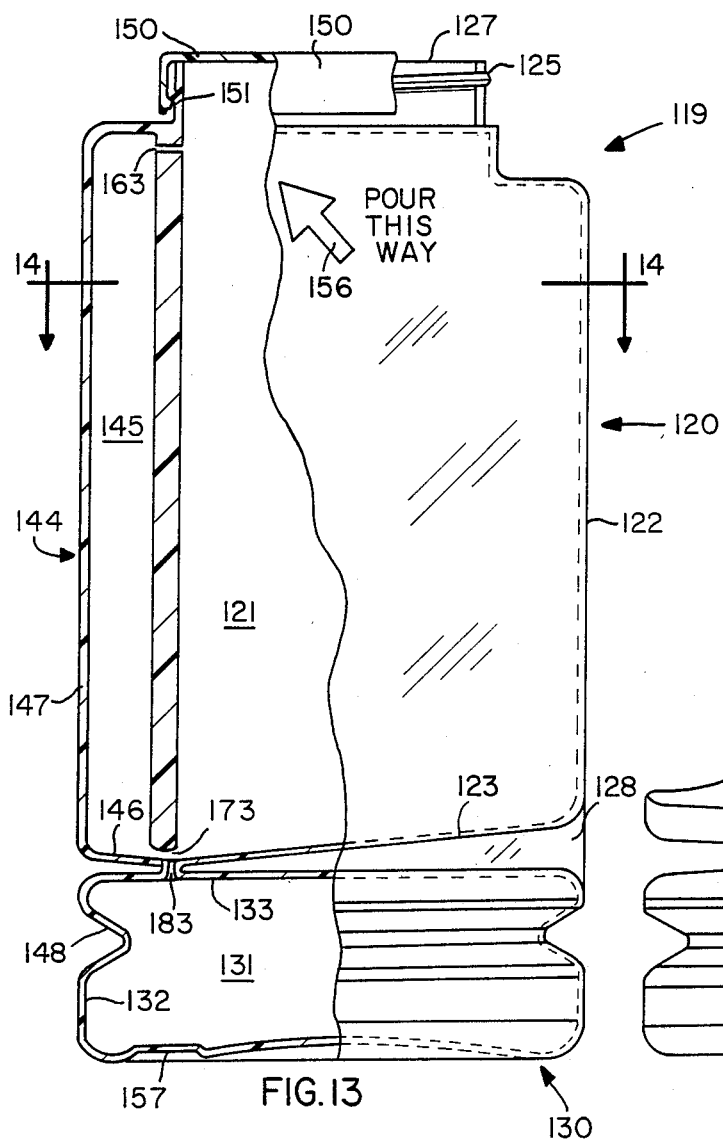
FIG. 13 is a partial cross-sectional front view of a liquid aliquoting apparatus having one aliquot measurement chamber according to one embodiment of this invention.
Figure 15:
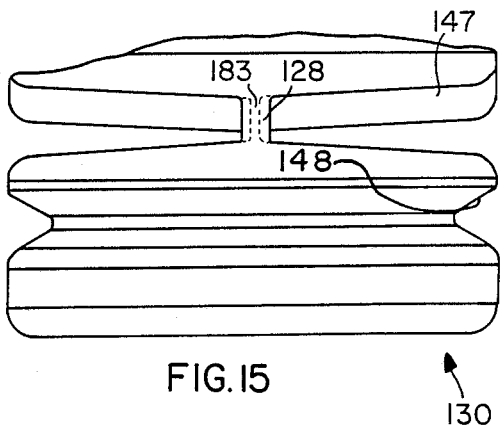
FIG. 15 is a partial side view of a lower portion of the liquid aliquoting apparatus along line 14—14, as shown in FIG. 13.

FIGS. 13–15 and FIGS. 16–18 show two similar embodiments of a liquid aliquoting apparatus according to this invention. FIGS. 13–15 show a liquid aliquoting apparatus having one liquid collection chamber, one aliquot measurement container and one aliquot storage chamber whereas FIGS. 16–18 show a liquid aliquoting apparatus having one liquid collection container with a separating wall, two aliquot measurement chambers and two aliquot storage chambers. Since the general design is similar for the embodiments as shown in FIGS. 13–15 and FIGS. 16–18, the remaining description of this invention is generally directed to the embodiment as shown in FIGS. 16–18. Any differences between the two embodiments will be discussed.

Liquid aliquoting apparatus 119 is used for obtaining an aliquot of a series of liquid samples. Liquid collection container 120 generally includes collection container walls 122, collection container bottom 123 and an upper portion, all of which define liquid collection chamber 121. The top portion of liquid collection container 120 forms opening 127. Opening 127 has a cross section large enough to accommodate a fluid sample intake into liquid collection chamber 121. In a preferred embodiment, the cross section of opening 127 is large enough to facilitate urine intake into liquid collection container 120 directly from human discharge. Opening 127 preferably has a circular cross section but can also have a polyhedron cross section or other suitable cross section.

Container top 150 is used to sealably close opening 127. Container top 150 has means for sealably engaging and mating container top 150 with an upper portion of liquid collection container 120. In one embodiment of this invention, container top 150 has internal container top threads 151 which sealably mate with external upper portion threads 125 of liquid collection container 120. It is apparent that container top threads 151 can be external relative to container top 150 and upper portion threads 125 can be internal relative to the upper portion. It is also apparent that snap-on caps or any other suitable firmly and sealably closing top may be used to close and seal liquid collection container 120.

One or more aliquot storage containers 130 each form an aliquot storage chamber 131 generally and preferrably positioned below liquid collection chamber 121, as shown in FIGS. 13–16. In another embodiment of this invention, each aliquot storage chamber 131 can be positioned adjacent liquid collection container 120. One or more aliquot measurement containers 144 each form an aliquot measurement chamber 145. Each aliquot measurement container 144 is preferably positioned generally vertical and adjacent liquid collection container 120. It is apparent that aliquot storage chamber 131 can be positioned adjacent either liquid collection container 120 or aliquot measurement container 144.

Vent means are positioned near a high point of each aliquot measurement container 144. Each aliquot measurement chamber 145 is in fluid communication with liquid collection chamber 120 through the vent means. In a preferred embodiment according to this invention, such vent means comprise one or more vent ports 163 positioned in a wall separating liquid collection container 121 and aliquot measurement chamber 145. Each vent port 163 is sized large enough to allow air, or another gas, to flow through each vent port 163. Each vent port 163 is also sized small enough to retain an aliquot measurement portion of the liquid sample within each aliquot measurement chamber 144 when liquid aliquoting apparatus 119 is tilted to discharge a liquid collection portion of the liquid sample from liquid collection chamber 120.

In general, liquid collection chamber 121 is filled with a liquid sample and an aliquot measurement portion of the liquid sample flows into aliquot measurement chamber 145. The liquid sample and aliquot measurement portion of the liquid sample seek an equilibrium level within liquid collection chamber 121 and aliquot measurement chamber 145. Vent port 163 preferably has a round or circular cross section with a vent port diameter in a range from about 3/128 inch to about 5/128 inch. A vent port diameter of about 1/32 inch has been determined as the most preferred.

Fill means are positioned in a region of a low point of each aliquot measurement container 144. Each aliquot measurement chamber 145 is in fluid communication with liquid collection chamber 120 through the fill means. In a preferred embodiment according to this invention, the fill means comprise at least one fill port 173 sized large enough to allow the liquid sample to seek an equilibrium level within liquid collection chamber 121 and each aliquot measurement chamber 145. Fill port 173 is sized small enough to retain an aliquot measurement portion of the liquid sample within each aliquot measurement chamber when liquid aliquoting apparatus 119 is tilted to discharge a liquid collection portion of the liquid sample from liquid collection chamber 121. Fill port 173 preferably has a round or circular cross section with a fill port diameter in a range from about 3/64 inch to about 5/64 inch, preferably about 1/16 inch.

Drain means are positioned at the low point of each aliquot collection chamber 145 and liquid collection chamber 121. Each aliquot measurement chamber 145 is in fluid communication with each corresponding aliquot storage chamber 131. In a preferred embodiment according to this invention, the drain means comprise one or more drain ports 183 each sized small enough to retain the liquid sample in each aliquot measurement chamber 145 and liquid collection chamber 121. Drain port 183 is also sized large enough to allow the liquid sample to flow through drain port 183 into each corresponding aliquot measurement chamber 145 when the volume displacement means are activated. Drain port 183 preferably has a round or circular cross section with a drain port diameter in a range from about 3/100 inch to about 5/100 inch, preferably about 1/25 inch.

Vent port 163, fill port 173 and drain port 183 each have a cross-sectional shape and dimensions sized according to the principles of fluid mechanics such that each respective port will effectively operate as valve means for allowing gas or air to flow through the port when liquid aliquoting apparatus 119 stands upright and for preventing the liquid sample from flowing through the port when liquid aliquoting apparatus 119 is tilted to discharge a liquid collection portion of the liquid sample from liquid collection chamber 121. Thus vent port 163, fill port 173 and drain port 183 can have various cross-sectional shapes according to the variable values of defined parameters including surface tension, temperature and fluid viscosity. The depth of each port may also be varied to control a desired valving effect of the port. It is apparent that vent port 163, fill port 173 and/or drain port 183 can be replaced with another suitable check valve or the like.

Liquid aliquoting apparatus 119 further comprises volume displacement means which are used to discharge a fluid from each aliquot storage chamber 131. Once the aliquot measurement portion of the liquid sample is retained within aliquot measurement chamber 145 and the liquid collection portion of the liquid sample is discharged from liquid collection chamber 121, the volume displacement means are activated to intake the aliquot measurement portion of the liquid sample from each aliquot measurement chamber 145.

In a preferred embodiment according to this invention, the volume displacement means comprise a collapsible aliquot storage container 130. Aliquot storage container 130 preferably has one or more bellowed sides for collapsing aliquot storage container 130. In the embodiment as shown in FIGS. 13 and 15-17, aliquot storage container 130 has bellowed sides about the entire periphery of liquid aliquoting apparatus 119. Bellows 148 may extend along the entire height of aliquot storage container 130. Bellows 148 may also extend along only a portion of the height of aliquot storage container 130 so that when aliquot storage container 130 is collapsed, the entire volume of aliquot storage chamber 131 is not displaced. It is apparent that the volume displacement of aliquot storage chamber 131 can also be accomplished with pressurized air, a bladder, or other suitable volume displacement mechanisms.

In a preferred embodiment according to this invention, liquid collection container 120 has collection container bottom 123 sloped downward toward fill port 173, or another suitable fill means. For additional support to liquid collection container 120, one or more supporting ribs 128 are secured between collection container bottom 123 and storage container top wall 133 of aliquot storage container 130.

In a preferred embodiment of this invention, funnel adapter 154 has convergent end 155 which is sealably attached to container top 150. Funnel adapter 154 is in communication with liquid collection chamber 121. It is apparent that other funnels having various inlet shapes can be used to accommodate fluid intake into liquid collection chamber 121. Particularly, a funnel shaped as shown in FIG. 17 can be used for urine intake directly from human discharge.

When discharging the liquid collection portion of the liquid sample from liquid collection chamber 121, liquid aliquoting apparatus 119 must be tipped or tilted in a certain direction in order to retain the aliquot measurement portion of the liquid sample within each aliquot measurement chamber 145. If liquid aliquoting apparatus 119 is not tipped or tilted in such direction, then as the liquid collection portion of the liquid sample is discharged from liquid collection chamber 121 the aliquot measurement portion of the liquid sample within each aliquot measurement chamber 145 will empty through each corresponding fill port 173 then drain out of liquid collection chamber 121. Thus, collection container wall 122 should have graphic instructions displayed on one or more collection container walls 122 of liquid collection container 120. The graphic instructions indicate a direction in which liquid aliquoting apparatus 119 must be tipped in order to retain the aliquot measurement portion of the liquid sample within each aliquot storage chamber 131. Such graphic instructions preferably include a directional arrow and/or language instructing a user how to properly tip or tilt and operate liquid aliquoting apparatus 119.

In a preferred embodiment, aliquot container bottom 146 and/or aliquot container side wall 147 of aliquot storage container 130 has one or more indents 157 or nipples 158 for accessing each aliquot storage chamber 131. It is apparent that other access means which can be cut or punctured or a suitable valve can be used to access the aliquot measurement portion of the liquid sample within each aliquot storage chamber 131.

In one preferred embodiment of this invention, the overall horizontal cross-sectional shape of liquid aliquoting apparatus 119 is rectangular. In such rectangular liquid aliquoting apparatus 119, one aliquot storage chamber 131 can occupy a corner section of liquid aliquoting apparatus 119 as shown in FIGS. 13 and 14. In another preferred embodiment of this invention, the overall horizontal cross-sectional shape of liquid aliquoting apparatus 119 is round or circular. In such cylindrical liquid aliquoting apparatus 119, at least one aliquot storage chamber can occupy an arc segment of liquid collection container 120. It is apparent that the overall horizontal cross-sectional shape can be any other suitable shape.

The cross-sectional shapes of liquid collection container 120 and aliquot measurement container 144 are preferably constant along the height of liquid aliquoting apparatus 119. However, such cross sections can also vary along the height of liquid aliquoting apparatus 119. In a preferred embodiment of this invention, an aliquot measurement volume of each aliquot measurement chamber 145 is in a range from about 1 percent to about 50 percent, preferably about 3 percent to about 5 percent, of the liquid collection volume of liquid collection chamber 121.

In an embodiment of this invention having a plurality of aliquot measurement chambers 145, one or more separating walls 124 are positioned between collection container walls 122. Collection container walls 122 span from collection container bottom 123 of liquid collection container 120 upward to less than about one-half of the height of liquid collection chamber 121. Each separating wall 124 forms a number of liquid collection containers 12 equal to the number of aliquot measurement containers 144. Separating wall 124 is also used to prevent the liquid sample from mixing and thus draining disproportional amounts of the liquid sample in each aliquot storage chamber 131.

A process for obtaining a percentage aliquot sample of a constant or variable volume from liquid aliquoting apparatus 119 as shown in FIGS. 13-18 includes introducing a liquid sample into liquid collection container 120. Once the aliquot measurement portion of the liquid sample flows from liquid collection chamber 121 into each aliquot measurement container 144 and a level of the liquid sample hydrostatically balances between liquid collection container 120 and each aliquot measurement container 144, liquid aliquoting apparatus 119 is tipped or tilted so that the liquid collection portion of the liquid sample within liquid collection chamber 120 is discharged and the aliquot measurement portion of the liquid sample within each aliquot measurement chamber 145 is retained. Liquid aliquoting container 119 is then returned to a generally vertical and upright position. Bellows 148 are compressed or other volume displacement means are activated to discharge at least a portion of the gas in aliquot storage container 130. Finally, bellows 148 or volume displacement means are expanded to draw the remaining aliquot measurement portion of the liquid sample from each aliquot measurement chamber 145 into each corresponding aliquot storage container 130.

It is apparent that the apparatus of this invention may be constructed in many sizes to accommodate a wide range of volumes of serial samples and aliquot measured amounts, as well as constructed of a wide variety of materials, such as polyethylene, polystyrene, polypropylene, and the like. It is also readily apparent that different parts of the apparatus may be constructed of different materials having quite different properties, such as construction of aliquot storage chambers from a flexible material with construction of sample collection chambers and valve components of a rigid material.

This invention provides the means for different treatments of a plurality of measured aliquot amounts of serial samples in the aliquot storage chambers. A different chemical or other preservative may be added to each of the plurality of aliquot storage chambers. The preservative treatment is more effective in the apparatus of this invention since only a small portion, in the order of a few percent, of the entire serial sample must be so treated. This further makes feasible different preservative methods than currently practiced with large sample volumes. For example, a suitable antibiotic agent or aminoglycoside antibiotic, such as gentamicin, may be added to at least one of the aliquot storage chambers in an amount sufficient to prevent undesired bioactivity in the aliquot storage amount in that aliquot storage chamber. This is especially important with respect to biological sampling, particularly urine sampling, since the appropriate antibiotic will not contaminate the sample nor alter the test results. Even when conventional acid preservatives are utilized, the preservation of only a small volume of the total serial sample allows different techniques to be used than the current provision of a quantity of liquid in the bottom of the sample container. For example, a sponge saturated with preservative acid, avoiding liquid acid, may be placed in the aliquot storage chamber which cannot be accessed by a patient. Also, the antibiotic in a liquid form can be evaporated leaving a solid form on one or more inner wall surfaces of aliquot storage container 130.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A liquid aliquoting apparatus for obtaining an aliquot of a series of liquid samples comprising: a liquid collection container forming a liquid collection chamber, a top portion of said liquid collection container forming an opening, said opening having a cross section large enough to accommodate a fluid sample intake into said liquid collection chamber, at least one aliquot storage container, each one forming an aliquot storage chamber below said liquid collection chamber, at least one generally vertical aliquot measurement container, each one forming an aliquot measurement chamber;

vent means positioned at a high point of each said aliquot measurement container, each said aliquot measurement chamber in fluid communication with said liquid collection chamber through said vent means;

fill means positioned in a region of a low point of each said aliquot measurement container and said liquid collection container, each said aliquot measurement chamber in fluid communication with said liquid collection chamber through said fill means;

drain means positioned at said low point of each said aliquot measurement container and said liquid collection container, each said aliquot measurement chamber in fluid communication with each corresponding said aliquot storage chamber; and volume displacement means for discharging a fluid from each said aliquot storage chamber and intaking a liquid sample from each corresponding said aliquot measurement chamber.

2. A liquid aliquoting apparatus according to claim 1 wherein said volume displacement means further comprise said aliquot storage container being collapsible.

3. A liquid aliquoting apparatus according to claim 2 wherein at least one side of said aliquot storage container has bellows.

4. A liquid aliquoting apparatus according to claim 1 wherein said liquid collection container has a liquid collection container bottom sloped downward toward said fill means.

5. A liquid aliquoting apparatus according to claim 4 further comprising a supporting rib secured between said liquid collection container bottom and an aliquot container top of said aliquot storage container.

6. A liquid aliquoting apparatus according to claim 1 further comprising a container top and engaging means for sealably mating said container top with an upper portion of said liquid collection container.

7. A liquid aliquoting apparatus according to claim 6 wherein said engaging means further comprise said container top having container top threads and said upper portion having upper portion threads sealably mateable with said container top threads.

8. A liquid aliquoting apparatus according to claim 6 further comprising liquid sample inlet means sealably attached to said container top and in communication with said liquid collection chamber.

9. A liquid aliquoting apparatus according to claim 8 wherein said liquid sample inlet means further comprise funnel means having a convergent end sealably attached to said container top.

10. A liquid aliquoting apparatus according to claim 1 further comprising graphic instruction means positioned on at least one liquid collection container side of said liquid collection container, said graphic instruction means indicating a direction in which the liquid aliquoting apparatus must be tipped to retain an aliquot measurement portion of said liquid sample within each said aliquot storage chamber.

11. A liquid aliquoting apparatus according to claim 10 wherein said graphic instruction means further comprise a directional arrow and language means for instructing a user how to properly tip and operate the liquid aliquoting apparatus.

12. A liquid aliquoting apparatus according to claim 1 wherein at least one of an aliquot container bottom and an aliquot container side wall of said aliquot storage container has access means for accessing each said aliquot storage chamber.

13. A liquid aliquoting apparatus according to claim 12 wherein said access means further comprise at least one indent in said at least one of an aliquot container bottom and an aliquot container side wall.

14. A liquid aliquoting apparatus according to claim 1 wherein an overall horizontal cross-sectional shape of the liquid aliquoting apparatus is rectangular.

15. A liquid aliquoting apparatus according to claim 14 further comprising one said aliquot storage chamber occupying a corner section of said liquid aliquoting apparatus.

16. A liquid aliquoting apparatus according to claim 1 wherein an overall horizontal cross-sectional shape of the liquid aliquoting apparatus is round.

17. A liquid aliquoting apparatus according to claim 1 wherein said cross section of said opening is large enough to facilitate urine intake into said liquid collection container directly from human discharge.

18. A liquid aliquoting apparatus according to claim 1 wherein said vent means further comprise at least one vent port, each said vent port sized large enough to allow air to flow through each said vent port, and each said vent port sized small enough to retain an aliquot measurement portion of said liquid sample within each said aliquot measurement chamber when the liquid aliquoting apparatus is tilted to discharge a liquid collection portion of said liquid sample from said liquid collection chamber.

19. A liquid aliquoting apparatus according to claim 18 wherein said vent port has a round cross section with a vent port diameter in a range from about 3/128 inch to about 5/128 inch.

20. A liquid aliquoting apparatus according to claim 19 wherein said vent port diameter is about 1/32 inch.

21. A liquid aliquoting apparatus according to claim 1 wherein said fill means further comprise at least one fill port, each said fill port sized large enough to allow said liquid sample to seek an equilibrium level within said liquid collection chamber and each said aliquot measurement chamber, and each said fill port sized small enough to retain an aliquot measurement portion of said liquid sample within each said aliquot measurement chamber when the liquid aliquoting apparatus is tilted to discharge a liquid collection portion of said liquid sample from said liquid collection chamber.

22. A liquid aliquoting apparatus according to claim 21 wherein said fill port has a round cross section with a fill port diameter in a range from about 3/64 inch to about 5/64 inch.

23. A liquid aliquoting apparatus according to claim 22 wherein said fill port diameter is about 1/16 inch.

24. A liquid aliquoting apparatus according to claim 1 wherein said drain means further comprise a drain port sized small enough to retain said liquid sample in each said aliquot measurement chamber and said liquid collection chamber, and said drain port sized large enough to allow said liquid sample to flow through said drain port into each said aliquot measurement chamber when said volume displacement means are activated.

25. A liquid aliquoting apparatus according to claim 24 wherein said drain port has a round cross section with a drain port diameter in a range from about 3/100 inch to about 5/100 inch.

26. A liquid aliquoting apparatus according to claim 25 wherein said drain port diameter is about 1/25 inch.

27. A liquid aliquoting apparatus according to claim 1 wherein an aliquot measurement volume of each said aliquot measurement chamber is in a range from about 1 percent to about 50 percent of a liquid collection volume of said liquid collection chamber.

28. A liquid aliquoting apparatus according to claim 27 wherein said range is about 3 percent to about 5 percent.

29. A liquid aliquoting apparatus according to claim 1 further comprising an aminoglycoside antibiotic stored within said at least one aliquot storage chamber.

30. A liquid aliquoting apparatus according to claim 29 wherein said aminoglycoside antibiotic in a liquid form is evaporated leaving a solid form of said aminoglycoside antibiotic on at least one inner wall surface of said aliquot storage container.

31. A liquid aliquoting apparatus according to claim 29 wherein said aminoglycoside antibiotic is gentamicin.

32. A liquid aliquoting apparatus according to claim 31 wherein said gentamicin in a liquid form is evaporated leaving a solid form of said gentamicin on at least one inner wall surface of said aliquot storage container.

33. A liquid aliquoting apparatus according to claim 1 further comprising at least one separating wall positioned between collection container walls of said liquid collection container from a liquid collection container bottom up to less than about one-half of a height of said liquid collection chamber, said at least one separating wall forming a first number of liquid collection containers equal to a second number of said at least one aliquot measurement container.

34. A liquid aliquoting apparatus for obtaining an aliquot series of liquid samples comprising: a liquid collection container forming a liquid collection chamber, a top portion of said liquid collection container forming an opening, said opening having a cross section large enough to accommodate a fluid sample intake into said liquid collection chamber, an aliquot storage container forming an aliquot storage chamber below said liquid collection chamber, a generally vertical aliquot measurement container forming an aliquot measurement chamber;

vent means positioned at a high point of said aliquot measurement container, said aliquot measurement chamber in fluid communication with said liquid collection chamber through said vent means;

fill means positioned in a region of a low point of said aliquot measurement chamber and said liquid collection container, said aliquot measurement chamber in fluid communication with said liquid collection chamber through said fill means;

drain means positioned at said low point of said aliquot measurement chamber and said liquid collection container, said aliquot measurement chamber in fluid communication with each corresponding said aliquot storage chamber; and volume displacement means for discharging a fluid from said aliquot storage chamber and intaking a liquid sample from said aliquot measurement chamber.

35. A liquid aliquoting apparatus according to claim 34 wherein said volume displacement means further comprise said aliquot storage container being collapsible.

36. A liquid aliquoting apparatus according to claim 35 wherein at least one side of said aliquot storage container has bellows.

37. A liquid aliquoting apparatus according to claim 34 wherein said liquid collection container has a liquid collection container bottom sloped downward toward said fill means and a supporting rib secured between said liquid collection chamber bottom and an aliquot container top of said aliquot container.

38. A liquid aliquoting apparatus according to claim 34 further comprising a container top and engaging means for sealably mating said container top with an upper portion of said liquid collection container.

39. A liquid aliquoting apparatus according to claim 38 wherein said engaging means further comprise said container top having container top threads and said upper portion having upper portion threads sealably mateable with said container top threads.

40. A liquid aliquoting apparatus according to claim 38 further comprising liquid sample inlet means sealably attached to said top and in communication with said liquid collection chamber.

41. A liquid aliquoting apparatus according to claim 40 wherein said liquid sample inlet means further comprise funnel means and a convergent end of said funnel means sealably attached to said top.

42. A liquid aliquoting apparatus according to claim 34 further comprising graphic instruction means positioned on at least one liquid collection container side of said liquid collection container, said graphic instruction means indicating a direction in which the liquid aliquoting apparatus must be tipped to retain said liquid sample within said aliquot storage chamber.

43. A liquid aliquoting apparatus according to claim 42 wherein said graphic instruction means further comprise a directional arrow and language means for instructing a user how to properly tip and operate the liquid aliquoting apparatus.

44. A liquid aliquoting apparatus according to claim 34 wherein at least one of an aliquot container bottom and an aliquot container side wall of said aliquot storage container has access means for accessing said aliquot storage chamber.

45. A liquid aliquoting apparatus according to claim 44 wherein said access means further comprise at least one indent in said at least one of an aliquot container bottom and an aliquot storage container side wall.

46. A liquid aliquoting apparatus according to claim 34 wherein an overall horizontal cross-sectional shape of the liquid aliquoting apparatus is rectangular.

47. A liquid aliquoting apparatus according to claim 46 wherein said aliquot storage chamber is vertically positioned in a corner section of said liquid aliquoting apparatus.

48. A liquid aliquoting apparatus according to claim 34 wherein an overall horizontal cross-sectional shape of the liquid aliquoting apparatus is round.

49. A liquid aliquoting apparatus according to claim 34 wherein said cross section of said opening is large enough to facilitate urine intake into said liquid collection container directly from human discharge.

50. A liquid aliquoting apparatus according to claim 34 wherein said vent means further comprise a vent port sized large enough to allow air to flow through said vent port, and said vent port sized small enough to retain an aliquot measurement portion of said liquid sample within said aliquot measurement chamber when the liquid aliquoting apparatus is tilted to discharge a liquid collection portion of said liquid sample from said liquid collection chamber.

51. A liquid aliquoting apparatus according to claim 50 wherein said vent port has a round cross section with a vent port diameter in a range from about 3/128 inch to about 5/128 inch.

52. A liquid aliquoting apparatus according to claim 51 wherein said vent port diameter is about 1/32 inch.

53. A liquid aliquoting apparatus according to claim 34 wherein said fill means further comprise a fill port sized large enough to allow said liquid sample to seek an equilibrium level within said liquid collection chamber and said aliquot measurement chamber, and said fill port sized small enough to retain an aliquot measurement portion of said liquid sample within said aliquot measurement chamber when the liquid aliquoting apparatus is tilted to discharge a liquid collection portion of said liquid sample from said liquid collection chamber.

54. A liquid aliquoting apparatus according to claim 53 wherein said fill port has a round cross section with a fill port diameter in a range from about 3/64 inch to about 5/64 inch.

55. A liquid aliquoting apparatus according to claim 54 wherein said fill port diameter is about 1/16 inch.

56. A liquid aliquoting apparatus according to claim 34 wherein said drain means further comprise a drain port sized small enough to retain said liquid sample in said aliquot measurement chamber and said liquid collection chamber, and said drain port sized large enough to allow said liquid sample to flow through said drain port into said aliquot measuring chamber when said volume displacement means is activated.

57. A liquid aliquoting apparatus according to claim 56 wherein said drain port has a round cross section with a drain port diameter in a range from about 3/100 inch to about 5/100 inch.

58. A liquid aliquoting apparatus according to claim 57 wherein said drain port diameter is about 1/25 inch.

59. A liquid aliquoting apparatus according to claim 34 wherein an aliquot measurement volume of said aliquot measurement chamber is in a range from about 1 percent to about 50 percent of a liquid collection volume of said liquid collection chamber.

60. A liquid aliquoting apparatus according to claim 59 wherein said range is about 3 percent to about 5 percent.

61. A liquid aliquoting apparatus according to claim 34 further comprising an aminoglycoside antibiotic stored within said aliquot storage chamber.

62. A liquid aliquoting apparatus according to claim 61 wherein said aminoglycoside antibiotic in a liquid form is evaporated leaving a solid form of said aminoglycoside antibiotic on at least one inner wall surface of said aliquot storage container.

63. A liquid aliquoting apparatus according to claim 61 wherein said aminoglycoside antibiotic is gentamicin.

64. A liquid aliquoting apparatus according to claim 63 wherein said gentamicin in a liquid form is evaporated leaving a solid form of said gentamicin on at least one inner wall surface of said aliquot storage container.

* * * * *